United States Patent [19]
Litwak et al.

[11] Patent Number: 5,092,572
[45] Date of Patent: Mar. 3, 1992

[54] ALLOGRAFT VISE

[75] Inventors: Alfred A. Litwak, Sea Bright; Alfred A. Litwak, Collingswood, both of N.J.

[73] Assignee: Anstat, Inc., Ocean, N.J.

[21] Appl. No.: 593,855

[22] Filed: Oct. 5, 1990

[51] Int. Cl.$^5$ ............................................. A61G 13/00
[52] U.S. Cl. .................... 269/328; 269/54.3; 269/71; 269/97; 269/253; 269/282
[58] Field of Search .................. 269/45, 75, 97, 54.3, 269/279-284, 328, 253, 71

[56] References Cited

U.S. PATENT DOCUMENTS

| | | | |
|---|---|---|---|
| 2,090,234 | 8/1937 | Robinowitz | 269/54.3 |
| 2,302,523 | 11/1942 | Borsella | 269/75 |
| 4,253,649 | 3/1981 | Hewson | 269/45 |
| 4,291,870 | 9/1981 | Warde | 269/279 |
| 4,461,284 | 7/1984 | Fackler | 269/45 |

Primary Examiner—Robert C. Watson
Attorney, Agent, or Firm—Robert M. Skolnik

[57] ABSTRACT

A vise for clamping and firmly holding allograph in place includes three adjustments which are accessible to the operating room staff from and within the sterile surgical field. The first adjustment includes a clamp to clamp the invention onto the standard operating room table. This first adjustment includes a clamp tightening handle and pivoting underside clamping surface which enables the vise to be mounted onto the operating table and secured onto the table by manipulations from above the surface of the operating room table and therefore, within the sterile field. The second adjustment includes an additional adjusting handle for angularly positioning the vise grip. The third adjustment includes another adjusting handle for opening and closing the vise. A variety of special purpose face plates for the two elements of the vise are provided to accommodate different surgical requirements. These face plates are removably inserted into the elements of the vise.

9 Claims, 4 Drawing Sheets

ALLOGRAFT VISE

FIELD OF THE INVENTION

This invention relates to a vise used in orthopedic surgery for holding an allograph firmly and adjustably in place to allow the surgeon to cut and shape the allograph and to perform the mounting on and removal of the vise from the operating room table as well as all the required adjustments and manipulations of the vise while maintaining the integrity of the sterile field. The surgeon need not lower his/her hands below the top of the table.

DESCRIPTION OF THE PRIOR ART

One of the requirements in orthopedic surgery is the cutting and shaping of bone in the use of bone implants. Bone implants are used for the following indications: (1) to hasten the healing of defects and cavities, e.g. the use of cancellous bone chips in the residual defect after curettage of a unicameral bone cyst; (2) to supplement the arthrodesis of joints, e.g., extraarticular arthrodesis of the tuberculous hip; (3) to achieve bony union in cases of delayed healing or pseudarthrosis arising after fracture, e.g., sliding or barrel stave grafts for nonunion of tibial shaft fractures; (4) to supplement the healing of certain fresh fractures for which open reduction and internal fixation are required, e.g., cancellous implants for fractures of both bones of the forearm in an adult; (5) to reconstruct major skeletal defects arising as a result of trauma, disease, or congenital malformation; (6) to reconstruct contour, e.g., replacement of calvarial defects after surgery for trauma by compact bone implants.

A variety of grafting techniques have been devised to meet the differing clinical requirements. The most frequent types of bone grafts are inlay grafts, onlay grafts and/or internal fixation, barrel stave grafts, sliding grafts, and application of cancellous chips. In addition, there are predicted grafts of two types, those with a bony base and muscle pedicle grafts. The pedicle technique applies strictly to autografts and was devised to circumvent devitalization thereby hastening healing.

Autografts are preferred for clinical use, since the cellular elements of bone allografts usually elicit a rejection response. Bone allografts do elicit new bone formation (osteoinduction) and serve as struts for the ingrowth of autologous bone (osteoconduction). As such, allografts are of great clinical use although they are always somewhat inferior to autografts.

For the most part, stored or processed bone allografts are used in human beings. Preservation methods include (1) refrigeration, (2) freezing, (3) freeze-drying, (4) boiling or autoclaving, (5) deproteinization, (6) decalcification, (7) any one of the above plus irradiation for sterilization, and (8) removal of marrow elements and replacement by autologous marrow. Such nonviable grafts mainly serve to stimulate and conduct new autologous bone formation.

SUMMARY OF THE INVENTION

A vise for clamping and firmly holding an allograph in place includes three adjustments which are accessible to the operating room staff from and within the sterile surgical field (i.e. from the top of the table). The first adjustment includes a table clamp to clamp the vise of the invention onto the standard operating room table. This first adjustment includes a lever connected to a pivoting clamping surface. The surgeon slides the vise of the invention onto the table so that the lever hits the lip of the table. As the vise continues to slide onto the table, the clamping surface pivots upward. There is a clamp tightening handle which is manipulated from above the surface of the operating room table and therefore, within the sterile field. This handle causes the clamping surface to engage the bottom of the table by pivoting same about a second pivot point also serves as a limiting and supporting surface for the edge of the table.

The second adjustment includes an additional adjusting handle for angularly positioning the vise grip. The third adjustment includes another adjusting handle for opening and closing the vise.

A variety of special purpose face plates for the two elements of the vise are provided so that the invention can accommodate different surgical requirements. These face plates can be removably inserted into the elements of the vise.

A principal object and advantage of this invention is the provision of an allograft vise in which all the required adjustments can be made to the instrument without breach of the sterile surgical field.

Another object of our invention is the provision of an allograft vise which can be angularly adjusted as required by the surgeon.

BRIEF DESCRIPTION OF THE DRAWINGS

These as well as further objects and advantages of the invention will become apparent to those skilled in the art from a review of the following detailed specification of our invention reference being made to the accompanying drawings in which.

DETAILED DESCRIPTION OF THE INVENTION

Figure 1:
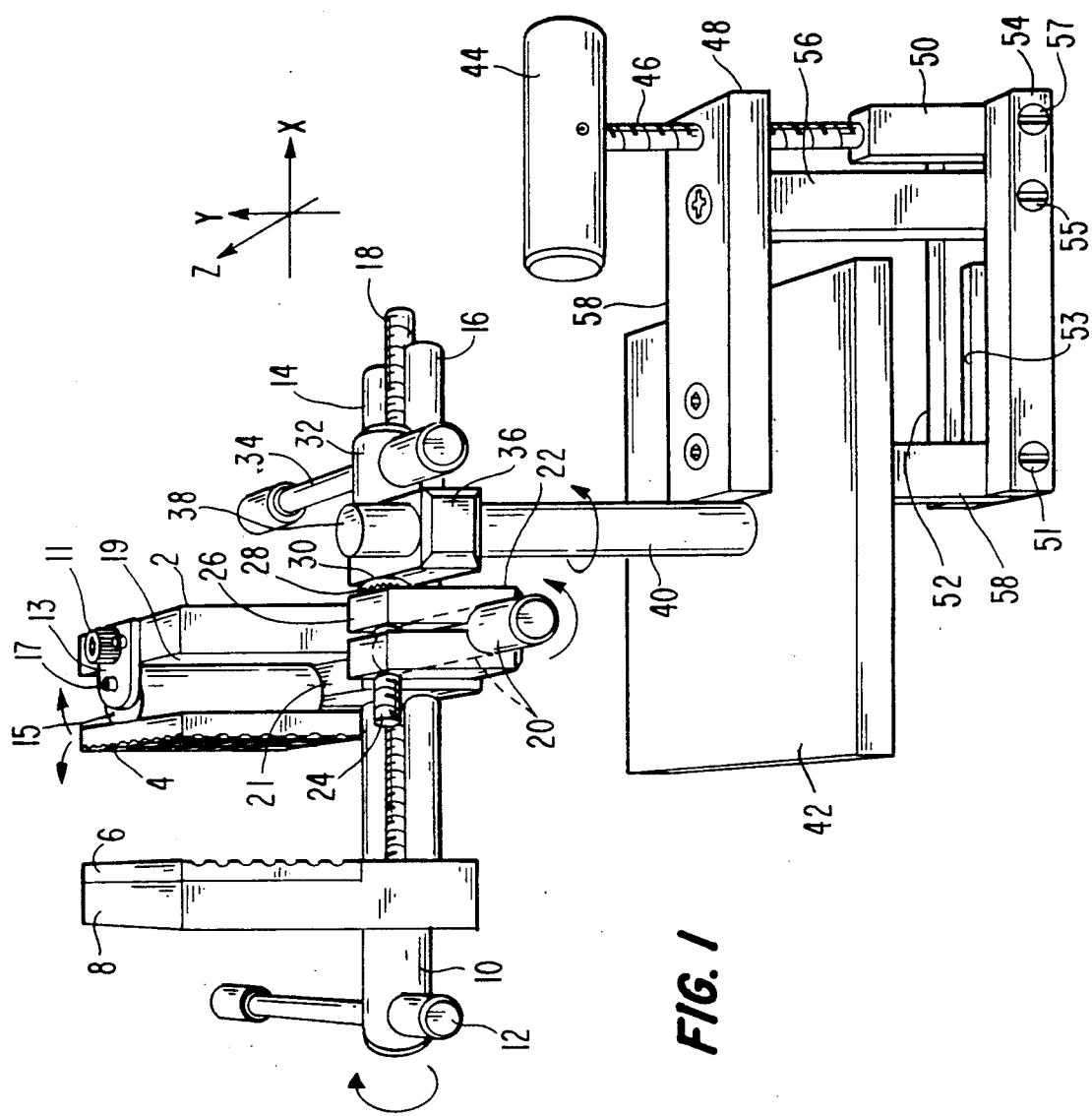
FIG. 1 is a perspective view of the vise of our invention.
Figure 4:
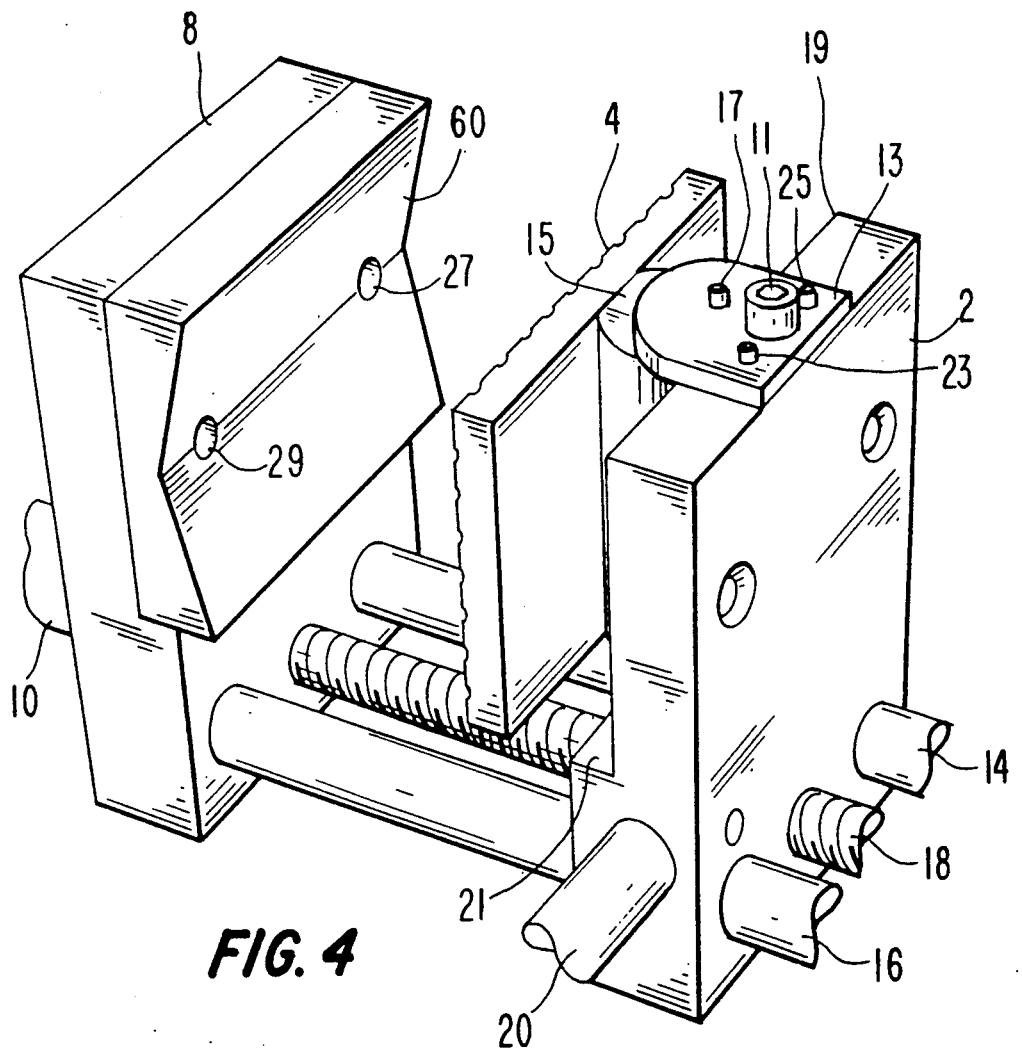
FIG. 4 is a perspective view of another special vise plate insert for use with FIG. 1.

FIG. 1 is a perspective view of the vise of our invention. As shown in FIG. 1, the vise portion of the invention includes two opposing vise plates 2 and 8. In the preferred embodiment, plate 2 is moveable and plate 8 is stationary. Each plate has a removeable face portion 4 and 6, respectively, mounted thereon. As will be further described herein, these face plates take different forms depending on the surgical procedures being employed. The plates 4 and 6 shown in FIG. 1 are formed with roughened supporting surfaces. These surfaces may be formed in a waffled pattern to assist in supporting allograft. Plate 4 is pivotally mounted against wall 19 on vise plate 2. The pivot mechanism permits the plate to swivel and takes the form a cylinder 15 attached to the plate 4. Cylinder 15 has an upper pin 17 and a lower pin (not shown) formed on the top and bottom surfaces of the cylinder. These pins fit into a hole in bracket 13 and another hole (not shown) in the ledge 21 in vise plate 2. Bracket 13 is removably fastened to vise plate 2 via threaded knob 11. In practice, threaded knob 11 is removed thus freeing bracket 13. As can now be seen, cylinder 15 and thereby plate 4 can pivot or swivel about the axis of cylinder 13. As best seen in FIG. 4, two supporting pins 23 and 25 may be formed in the top of vise plate 2 to interfit within suitable holes in bracket 13 to prevent unwanted lateral movement of bracket 13.

The moveable vise plate 2 is securely mounted on three cylindrical bars, 14, 16 and 18. Bars 14 and 16 provide smooth sliding and support surfaces for plate 2. Bar 18 is threaded and cooperates with internal threads (not shown) formed in a bore in vise plate 2. A collar 10 is rotatably coupled to the threaded shaft 18. An adjusting handle 12 is mounted in collar 10 to cause the rotation of the collar and the threaded shaft and, thereby, the movement of vise plate 2 towards plate 8 slidably along the bars 14 and 16.

All of the elements thusfar described are further adjustably mounted so as to be angularly rotated with respect to the horizontal. This angular adjustment is provided by a shaft 20 which is connected to vise plate 2. A U-shaped collar 22 is adjustably mounted on shaft 20. The collar's 22 grip on shaft 20 can be tightened or loosened via threaded shaft 24 which passes through both of the arms of the U-shaped collar 22. One arm 26 of collar 22 has a serrated gripping outer surface 28 formed thereon. The serrations of surface 28 serve to grip with a complementary serrated surface on the arm 30 of another adjusting collar 36. The collar 36 is tightened or loosened about the upper portion 38 of another shaft 40. Threaded shaft 24 also passes through the arms of collar 36 to tighten or loosen the collar. A handle 34 is provided in collar 32 (connected to shaft 24) to rotate the shaft and thereby tighten or loosen both of the collars 22 and 36

Shaft 40 is fixedly mounted in table clamping and support plate 42. The support plate 42 provided a stable support surface for the invention and is intended to be clamped to the top surface of the standard operating room table. This clamping arrangement will now be described with reference to FIGS. 1 and 2.

As previously noted, the vise is required to be sterile and be capable of all required manipulations within the sterile surgical field. Accordingly, the clamping arrangement for support plate 42 provides a rotation handle 44 located above the plate. Handle 44 is connected to a threaded shaft 46. The shaft 46 passed through and is threadedly engaged with a threaded aperture in stationary bar 48 and, movably, into a non-threaded hole in the support block 50 of relatively larger diameter than the diameter of threaded shaft 46.

Figure 2:
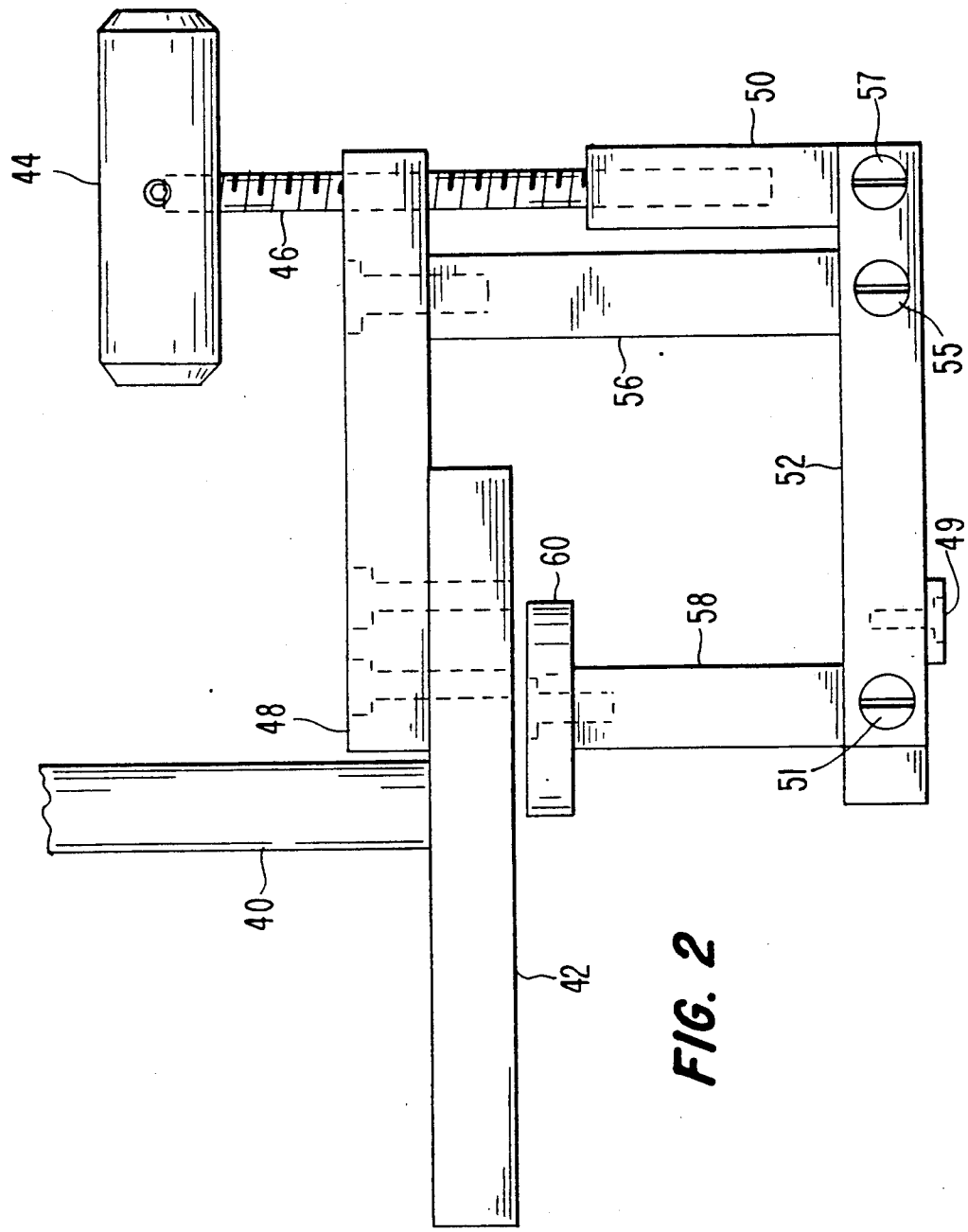
FIG. 2 is a side view of a portion of FIG. 1.

As best seen in FIGS. 1 and 2, three pivot points 51, 55 and 57 are provided. The first pivot point, 51 includes a screw threaded shaft for pivotal engagement with support shaft 58 and lever 53 between supporting bars 52 and 54. The lever 53 is connected to the shaft 58 and both the shaft and the lever can pivot about shaft 51. A clamping surface 60 is affixed to shaft 58. This clamping surface is designed to interfit and be clamped onto the underside of the operating room table.

The second pivot 55 is another threaded shaft mounted between bars 52 and 54 and through an aperture in the bottom of shaft 56. This pivot 55 permits the shaft 56 to act as a fulcrum for forces exerted via handle 44 on clamping surface 60. In addition shaft 56 acts to limit the amount of travel of the side wall of the operating room table beneath the upper clamping and support surface 42.

The third pivot 57 is another threaded shaft mounted between bars 52 and 54 and through an aperture in the bottom of shaft 50. As will now be seen, clockwise rotation of handle 44 in the threaded aperture in bar 48 causes threaded shaft 46 to exert a downward force (as shown in FIG. 2) in the hole in shaft 50 and thereby, on pivot 57. This downward force at pivot 57 is translated to an upward force and pivot 51 because of the fulcrum at pivot 55. The threaded engagement of threaded shaft 46 into the threaded aperture in bar 48 thus enables the shaft 46 to move freely upwardly and downwardly in the hole in shaft 50.

To affix the vise to the table without the surgeon lowering his/her hands below the top of the table, the lever 53 is lifted upwards to its vertical position thus causing shaft 58 and surface 60 to a horizontal position (opposite to the positions shown in FIGS. 1 and 2). The vise is then slid on the table so that lever 53 hits the lip of the table. As the vise continues to slide over the table, lever 53 turns downward and shaft 58 and surface 60 upwards to the positions shown in FIG. 2. The limit of travel of the vise in sliding along the table is established by shaft 56. The lip of the table contacts shaft 56 thereby stopping the travel of the sliding vise assembly over the top of the table.

If desired, a (not shown) spring may be employed to ensure that the clamping surface 60 is biased to assume its horizontal position (and lever 53 its vertical position) when the clamp is not in use to ensure that there will be no need for any adjustment beneath the surface of the table during surgery.

As will now be seen, the bar 48 is tightened on the support plate 42 on the top of the table against the forces of support disc 60 being seated on the underside of the table.

Figure 3:
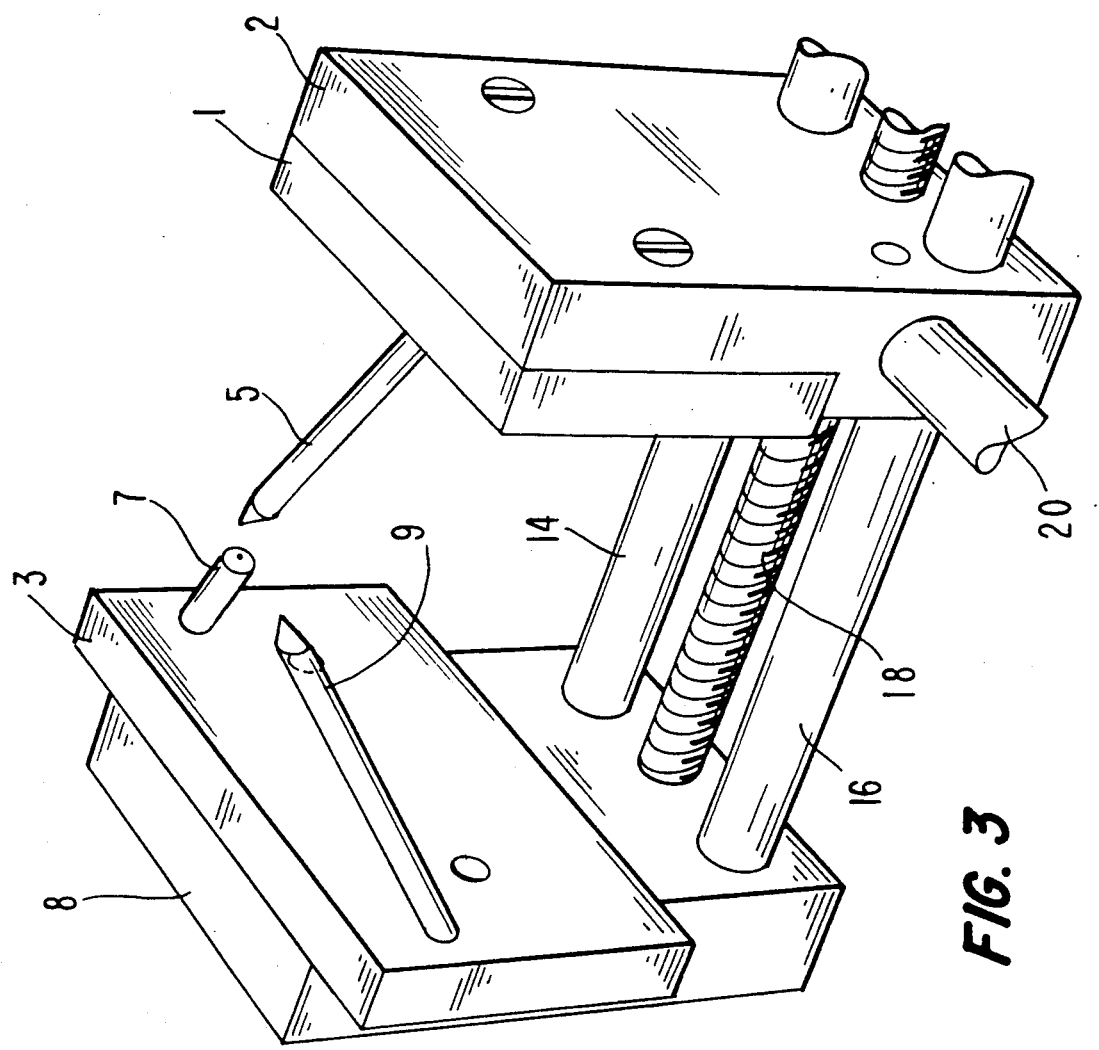
FIG. 3 is a perspective view of a special vise plate insert for use with FIG. 1.

FIG. 3 shows the special vise plates 1 and 3 used in a surgical procedure where support of the femur is required. These special face plates 1 and 3 have provide a sharp pointed tripod support for the femur. The tripod is formed at the ends of the spaced arms 5, 7 and 9.

A single arm 5 is extended upwardly from plate 1 and two arms 7 and 9 are similarly formed on plate 3. Each of the plates 1 and 3 are removably mounted in vise plates 8 and 2, respectively, as by screws.

FIG. 4 shows another alternative plate 60 affixed to vise plate 8 by screws 27 and 29. The "V" shaped plate 60 is used to support longer lengths of allograph in the notch of the "V" along the longitudinal axis of the allograph.

It will be apparent that modifications may be made by in the vise of this invention, incorporating different face plates, methods of attachment of same and different mechanisms; accordingly, what is sought to be protected is set forth in the appended claims.

I claim:

1. An allograft vise comprising: first and second vise gripping plates, means connected to said vise plates for moving said plates relative to each other and vary the distance between said plates; means connected to said vise plates for angularly adjusting the plane of said vise plates; clamping means connected to said angularly adjusting means for clamping said vise to a support surface, said means for moving said vise plates including a first manually rotatable handle, and rotatable threaded means connected to said first manually rotatable handle and to at least one of said vise plates whereby rotation of said handle causes rotation of said threaded means and movement of said vise plate; said means for angularly adjusting said vise plates including a first swivel support extending from one of said vise plates, first adjustable means connected to said swivel support for permitting said swivel support to rotate and a second manually rotatable handle connected to said first adjustable means for tightening and loosening said first adjustable means; said clamping means including a second support connected to said means for angularly adjusting said vise plates and a clamping surface adjustably coupled to said second support surface for clamping said vise to a working surface located between said second support surface and said clamping surface, said clamping surface being connected to a rotatable clamping surface support pivotally mounted for bringing said clamping surface into and out of engagement with said working surface; a third adjustable handle connected to said support surface and to said rotatable clamping surface support for adjusting the clamping force exerted by said clamping surface on said working surface.

2. The allograft vise of claim 1 wherein said vise gripping plates include respective removeable inserts, one of said inserts having a roughened flat surface and the other of said inserts having a notched surface for firmly supporting allograph in said notch.

3. The allograft vise of claim 1 wherein said vise gripping plates include respective removeable inserts, one of said inserts having an angularly extending pointed rod formed thereon and the other of said inserts having a pair of angularly extending pointed rods extending therefrom, said rods each extending towards each other for forming a tripod support for firmly supporting allograph between the ends of said rods.

4. The allograft vise of claim 1 wherein said first, second and third manually adjustable handles are all located within the sterile surgical field above a plane of said working surface.

5. An allograft vise comprising: first and second vise gripping plates, means connected to said vise plates for moving said plates relative to each other to vary the distance between said plates; means connected to said vise plates for angularly adjusting the plane of said vise plates; clamping means connected to said angularly adjusting means for clamping said vise to a support surface said clamping means being adjustable from above said support.

6. The vise of claim 1 wherein said rotatable clamping support and said third adjustable handle are pivotally mounted in a pair of parallel rails and further including a bar means connected to said support surface pivotally mounted in said parallel rails at a position between said rotatable clamping support and said third adjustable handle for permitting the forces exerted by said third adjustable handle to be transmitted to said clamping surface.

7. An allograft vise comprising: first and second vise gripping plates, means connected to said vise plates for moving said plates relative to each other to vary the distance between said plates; means connected to said vise plates for angularly adjusting the plane of said vise plates; clamping means connected to said angularly adjusting means for clamping said vise to a support surface said clamping means being adjustable from above said support surface; said clamping means including first and second clamping surfaces, said first clamping surface contacting the upper side of said support surface and said second clamping surface contacting the lower side of said support surface, means connected to said second clamping surface for pivoting said second clamping surface into and out of a position for engagement with said lower side of said support surface by contacting a portion of said support surface when said clamping means is being affixed to said support surface; connecting means connected to and pivotally mounting said second clamping surface; support bar means connected to said first clamping surface said bar means being pivotally mounted in said connecting means and adjustment handle means pivotally mounted in said connecting means for adjusting the clamping forces on said second clamping surface.

8. In an allograft vise for use in operating room surgical procedures having first and second vise gripping plates, means connected to said vise plates for moving said plates relative to each other and to vary the distance between said plates; means connected to said vise plates for angularly adjusting the plane of said vise plates; clamping means connected to said angularly adjusting means for clamping said vise to a support surface; the improvement comprising mounting means in at least one of said vise gripping plates for removably mounting an insert said mounting means including a first swivel support extending from said vise plate for supporting said insert and permitting said insert to rotate to compensate for allograph of differing configuration.

9. An allograft vise comprising: first and second vise gripping plates, means connected to said vise plates for moving said plates relative to each other and vary the distance between said plates; means connected to said vise plates for angularly adjusting the plane of said vise plates; said angular adjusting means including a manually rotatable handle connected to said angular adjusting means for tightening and loosening said angular adjusting means; at least two clamping means connected to said handle for holding said angular adjusting means in a desired position; serrated anchoring means connected to said clamping means for holding said clamping means in the desired position, all of said foregoing means being formed of sterilizable materials.

* * * * *